(12) United States Patent
Buchanan et al.

(10) Patent No.: US 9,271,907 B2
(45) Date of Patent: Mar. 1, 2016

(54) COMPOSITIONS AND METHODS FOR PROTECTION OF SKIN AGAINST THERMAL INSULT

(75) Inventors: Janice Paige Buchanan, Hattiesburg, MS (US); Laura Lynn Anderson, New Brunswick, NJ (US); Nicole Marie Mackey, Hattiesburg, MS (US); Robert Yeats Lochhead, Hattiesburg, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 760 days.

(21) Appl. No.: 12/932,622

(22) Filed: Mar. 1, 2011

(65) Prior Publication Data

US 2011/0217247 A1   Sep. 8, 2011

Related U.S. Application Data

(63) Continuation of application No. 61/339,184, filed on Mar. 1, 2010.

(51) Int. Cl.
| | |
|---|---|
| *A61K 8/02* | (2006.01) |
| *A61K 8/18* | (2006.01) |
| *A61K 8/24* | (2006.01) |
| *A61K 8/34* | (2006.01) |
| *A61K 8/41* | (2006.01) |
| *A61Q 17/04* | (2006.01) |
| *A61Q 19/00* | (2006.01) |
| *A61K 8/92* | (2006.01) |
| *A61K 8/19* | (2006.01) |
| *A61K 8/20* | (2006.01) |
| *A61K 8/23* | (2006.01) |
| *A61K 31/047* | (2006.01) |
| *A61K 31/695* | (2006.01) |
| *A61K 33/00* | (2006.01) |
| *A61K 33/02* | (2006.01) |
| *A61K 33/04* | (2006.01) |
| *A61K 33/06* | (2006.01) |
| *A61K 33/14* | (2006.01) |
| *A61K 33/42* | (2006.01) |

(52) U.S. Cl.
CPC ... *A61K 8/18* (2013.01); *A61K 8/19* (2013.01); *A61K 8/20* (2013.01); *A61K 8/23* (2013.01); *A61K 8/24* (2013.01); *A61K 8/34* (2013.01); *A61K 8/41* (2013.01); *A61K 8/92* (2013.01); *A61K 31/047* (2013.01); *A61K 31/695* (2013.01); *A61K 33/00* (2013.01); *A61K 33/02* (2013.01); *A61K 33/04* (2013.01); *A61K 33/06* (2013.01); *A61K 33/14* (2013.01); *A61K 33/42* (2013.01); *A61Q 17/04* (2013.01); *A61Q 19/00* (2013.01)

(58) Field of Classification Search
CPC ............ A61K 8/18; A61K 8/24; A61K 8/34; A61K 8/92; A61K 8/19; A61K 8/20; A61K 8/23; A61K 31/047; A61K 31/695; A61K 33/00; A61K 33/02; A61K 33/04; A61K 33/06; A61K 33/14; A61K 33/42; A61Q 17/04; A61Q 19/00
See application file for complete search history.

(56) References Cited

U.S. PATENT DOCUMENTS

| | | | | |
|---|---|---|---|---|
| 6,475,514 | B1 * | 11/2002 | Blitzer et al. ................. | 424/449 |
| 2009/0186055 | A1 * | 7/2009 | Dumousseaux et al. ...... | 424/401 |
| 2009/0258060 | A1 * | 10/2009 | Cleary et al. ................. | 424/448 |

* cited by examiner

*Primary Examiner* — Lezah Roberts
*Assistant Examiner* — Nannette Holloman
(74) *Attorney, Agent, or Firm* — Lawrence Arthur Schemmel

(57) ABSTRACT

The present invention provides novel topically-applied skin and face coating and paint compositions comprising near infrared reflecting pigments and hydrogels swollen with aqueous solution and/or with simulated sweat. The invention further provides methods of making and using the compositions. The novel compositions protect the skin of the wearer from damage due to intense external heat or thermal flux and simultaneously divert thermal energy to a complementary evaporative cooling mechanism. The compositions protect skin from external thermal fluxes, conform to skin chemistry, and are easy to apply and remove.

51 Claims, 2 Drawing Sheets

COMPOSITIONS AND METHODS FOR PROTECTION OF SKIN AGAINST THERMAL INSULT

CROSS-REFERENCE TO RELATED APPLICATION

This application claims priority from U.S. Provisional Patent Application Ser. No. 61/339,184 filed Mar. 1, 2010. The entirety of that provisional application is incorporated herein by reference.

STATEMENT OF GOVERNMENT SUPPORT

This invention was made with government support under Contract No. W911QY-09-C-0037 awarded by the United States Department of Defense (Army). The government may have certain rights in the invention.

FIELD OF THE INVENTION

This invention relates to the field of topically-applied skin and face coatings and more specifically to the field of skin and face paint compositions and methods of manufacture and use. The compositions comprise near infrared reflecting pigments and hydrogels swollen with aqueous solution and/or with simulated sweat, whereby the skin of the wearer is protected from damage due to intense external thermal flux.

BACKGROUND OF THE INVENTION

The present invention in a preferred embodiment utilizes novel compositions to be applied to a wearer's skin to protect the skin from external heat fluxes applied naturally or artificially. These compositions comprise reflecting pigments and hydrogels for simultaneously reflecting heat away from the skin and diverting thermal energy to a complementary evaporative cooling mechanism. Further, methods of making the compositions and methods of use are also disclosed.

Current technologies exist that provide skin and face paint having camouflage and/or thermal reflective characteristics. For example, U.S. Pat. No. 5,254,406 discloses a face paint material for application to the skin of the human body. The face paint comprises metallic particles embedded in a gel, such as petroleum jelly. This invention is directed to the avoidance of detection of a soldier's face by thermal imaging devices, but would not protect against the burning of skin by intense thermal flux because its metal particles would typically conduct heat to the surface of the skin and gels like petroleum jelly would be ignited by such a thermal flux, therefore exacerbating heat injury and burns.

U.S. patent application 20090081453 discloses a low emissive camouflage paint comprising metal flakes having thermal reflective properties. The metal flakes are coated in a colored coating that is transparent in the thermal radiation range. It is notable that in this disclosure the colored moiety is transparent in the thermal radiation range. Moreover, the application is directed to a skin paint that provides thermal camouflage by reflecting the human body's infrared signal back to the skin instead of outwards to an infrared detection device. The metal powders are thermally conducting and would be expected to conduct the heat of an external intense flux directly to the skin of the wearer. Such skin paints would be unlikely to protect the skin from damage caused by intense thermal fluxes.

Infrared reflective pigments are also disclosed in U.S. Pat. Nos. 6,174,360; 6,454,848; and 6,989,056. These disclosed pigments reflect heat in the near infrared region, typified by 0.001 to 3 microns. Such pigments are available commercially under the trade names Cool Colors™ and Eclipse™ IR Heat and Energy Saving Pigments from Ferro Corporation and Arctic infrared reflecting pigments from Shepherd Color Corporation. U.S. Pat. No. 5,811,180 discloses heat reflective pigments that mitigate or prevent ignition of combustible substances by near-infrared radiation. This patent does not teach one skilled in the art of camouflage 'make-up' or how to make or apply compositions to living skin for the purpose of meeting the much higher challenge of preventing a burn injury when the skin is exposed to a ballistic heat flux. U.S. Pat. Nos. 7,241,500 and 7,452,598 disclose shingles comprising infrared reflective pigments that mitigate the absorption of solar heat and have resistance to thermal stresses. These patents do not disclose use of thermally-reflective pigments in skin paints.

The use of hydrogels to prevent or extinguish fire is well-known. For example, U.S. patent application 20060157668 discloses fire-fighting compositions comprising a water-insoluble superabsorbent polymer, a colorant and an opacifier. Protection of structures from the effect of an explosion by covering all or part of the structure with a water gel is described in U.S. patent application 20080229969. The prevention of combustion by the application of a reversible or degradable superabsorbent polymer and water is disclosed in U.S. patent application 20070001156. Fire retardant compositions comprising the potassium salts of carboxylate polymers are disclosed in U.S. patent application 20070262290. Fire retarding and/or extinguishing compositions based on at least one water absorbing polymer are described in U.S. patent application 20070289752. U.S. patent application 20030159836 describes thermosensitive hydrogels that have low viscosity at ambient temperature that can gel or solidify at high temperature to act as fire extinguishers.

Based on the prior art, there exists a need for novel topically-applied paint compositions and methods that efficiently protect skin from external thermal fluxes, conform to skin chemistry, and are easy to apply and/or to remove. The present invention provides such compositions and methods.

SUMMARY OF THE INVENTION

The present invention provides for novel compositions of skin and face paints applied to a wearer to prevent or lessen burning of the skin by reflecting heat from the skin surface. The invention in a preferred embodiment provides for compositions that are designed to protect military and first responders from flash fire and other intense thermal flux conditions but can also be used to protect the skin of any wearer from burning due to an external heat source. The invention further provides for methods of making and using such compositions.

Some occupations exist, such as warfighters and firefighters, in which personnel can be exposed to intense thermal fluxes that can cause severe burns on exposed skin such as the face. In the case of warfighters, for example, such injuries are exacerbated by oil or wax-based camouflage face paint that can melt on the face and that may transfer heat to the facial tissue. The oils and waxes of commercial face paints can also ignite under these intense heat fluxes. As a result, there is a need to ameliorate or prevent damage to the skin by typical heat flux and additionally for such intense heat fluxes.

With the foregoing and other objects, features, and advantages of the present invention that will become apparent, the nature of the invention may be more clearly understood by reference to the following detailed description of the invention and to the appended claims.

BRIEF DESCRIPTION OF THE DRAWINGS

These drawings accompany the detailed description of the invention and are intended to illustrate further the invention and its advantages.

DETAILED DESCRIPTION OF THE INVENTION

Figure 1:
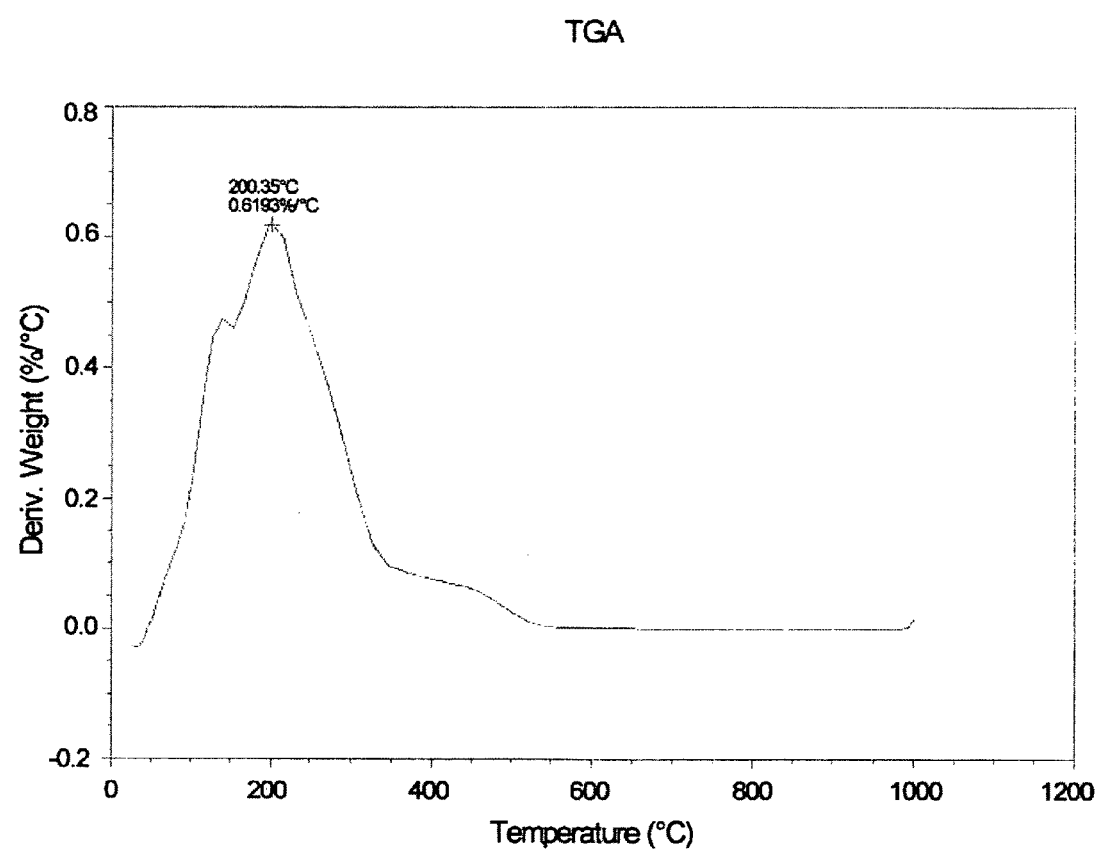
FIG. 1 is a graphical illustration of the rate of water loss from Pemulen TR-2 hydrogel sample prepared in simulated sweat under ballistic heating conditions using a TA instruments Q5000 TGA.

The present invention is directed to and provides novel compositions and use of skin and face paints comprising near infrared reflecting pigments and hydrogels, swollen with aqueous solution or preferably with simulated sweat, to protect the skin of a wearer from damage due to intense thermal flux from an external source. Further, it provides methods of making and of using such compositions. Optionally, the new skin paint compositions may be designed as camouflage face and body paint.

The compositions and methods of the present invention prevent or ameliorate burning of the skin by reflecting intense heat from the surface of the skin and simultaneously diverting thermal energy to a complementary evaporative cooling mechanism. Such intense heat can emanate from an external source, such as an explosion or a fireball. One preferred embodiment of the invention provides skin covering compositions that incorporate at least one near-infrared reflecting pigment to reflect the intense heat away from the skin that is protected therewith. Another embodiment of the present invention includes hydrogels in the compositions to remove heat by the evaporation of a volatile solvent such as water. It is desirable that the constituent elements of the topically-applied formulation confer desirable consumer attributes including but not limited to ease of spreading on the skin, substantivity to skin and hair, durability during the wearing period, and ease of removal after use.

It is preferred that the hydrogels should be compatible with the near-infrared reflective pigments. It is also preferred that the hydrogels should be compatible with but not substantially removed by perspiration. It is also preferable that the entire composition including hydrogels and pigments should be easily removed after use, or in the event of the skin being burned, by simply flushing with conventional soap and water or by employing a nonirritant fluid. The hydrogels preferably are swollen to between about 5 and 2000 times the volume of the polymer therein. The swelling volume can be calculated from measurement of the intrinsic viscosities of the hydrogels or from measurement of the critical overlap concentration of the polymers within the hydrogels.

The compositions and methods of the present invention comprise utilizing at least one pigment, including cosmetic pigment, near-infrared reflecting pigment, or combinations thereof and at least one hydrogel. Optionally, dispersants, surfactants, and emulsifiers can be added to aid the dispersion of the pigments, the maintenance of colloidal stability, and ease of spreading of the compositions on the skin. Surfactants aid in spreading the compositions on skin and include those from the Abex® family by Rhodia Novecare. Nonvolatile oils, humectants, and slip agents, or combinations thereof, may be included in the compositions for ease of spreading and substantivity of the compounds on skin. Dimethicone (HL88) or other suitable cosmetic or topically-applied silicone slip agent may be used. Volatile oils may be added to aid in and to confer good spreading and uniform coverage of the compositions on skin and then, desirably, to evaporate before use. A simulated sweat solution may be added that consists of an effective amount of chloride, sulfate, phosphate inorganic salt, or a combination thereof. Salts may be added to the compositions, through the simulated sweat solution, to adjust the rheology and also to confer compatibility with sweat. In addition, common film formers may be added to provide mechanical integrity to the resulting topically-applied coating, and standard combinations of anti-microbial agents and other preservatives are added to maintain acceptable shelf life. Film formers that may be used include, but are not limited to, sulfopolyesters, exemplified by the AQ® resins from Eastman Chemical Corporation, preferably AQ-38, AQ-55, AQ-48, and the hydrophobic polylactams exemplified by the Ganex® resins from International Specialty Products, preferably Ganex® V 216, and Ganex V 220.

The near infrared pigment of the invention should desirably reflect radiated heat in the range of wavelengths from about 0.001 microns to about 5 microns. Suitable pigments for use in the inventive compositions are available commercially under the trade names Cool Colors™ and Eclipse™ IR Heat and Energy Saving Pigments from Ferro Corporation, Arctic® infrared reflecting pigments from Shepherd Color Corporation, and ST series titanium dioxide dispersions from Kobo Products, Inc.

The hydrogels of the invention are materials that absorb water in relatively large proportions to their mass and release the water under the influence of heat. Suitable hydrogels are those that are formed from hydrophilic polymers and are swollen by water or aqueous solutions. Preferably one or a plurality of hydrogel-forming polymers should be selected from the group of products having high maximum swellability, such as those with the trade names Carbopol®, Pemulen®, Ultrez®, Luvigel®, Aristoflex®, and Sepigel®. Salt concentration (ionic strength) has a tremendous influence on hydrogel stability and integrity and will influence the combination and concentration of hydrogel polymers employed in composite formulations. Typical salts added to formulations are from the groups of inorganic chlorides, sulfates, and phosphates. Suitable dispersant surfactants, in addition to hydrogel polymers, which may also serve as surfactant and emulsifying polymers, include poloxamers sold by BASF under the trade name Pluracare® and Abex® surfactants sold by Rhodia Novecare, and DC-5225 from Dow Corning (as a formulation aid).

Volatile and non-volatile oils aid in spreading the composition on the skin. Suitable oils are volatile and non-volatile silicone oils. Dow Corning 245, 510 and 749 Fluid or HL88 by Barnett Products are examples of suitable silicone oils. Hydrocarbon oils such as dodecane can also be used, but silicone oils are preferred due to their low flammability in the near infrared flame region of the electromagnetic spectrum. The oils must be emulsified in the compositions. Suitable emulsifiers include glycerol mono-oleate, sold under the trade name Stepan GMO®, ammonium nonylphenol ether sulfate available from Rhodia under the trade name ABEX EP 110, and Pemulen® polymeric emulsifiers.

Film formers enhance the mechanical properties of the topically-applied coating, aid in the resistance to material transfer, and provide for water-resistant formulations. These film formers may be selected to provide a continuous film within the topically-applied coating, such as that from sulfonated polyesters, polyesteramides, silicones, or hardening wax or hydrocarbon block copolymeric elastomers carried by a volatile solvent. An example of a specific continuous film former that can be used is the AQ-48 resin from Eastman and Ganex® resin from International Specialty Polymers. Alternatively, a transfer-resistant film-former may be selected to not form a continuous film within the topically-applied coating, such as silsesquioxanes or MQ resins, which is formulated to provide all the positive attributes of a classical film-former while enhancing the film transfer resistance. Film formers are used alone or in combinations to tailor film properties.

Additional additives to the novel composite formulation include common preservatives and anti-microbial agents. These agents serve to extend the shelf life and user safety of cosmetic or topically-applied formulations. Methyl and propylparabens, methichloroisothiazolinone, and methylisothiazolinone are representative examples of preservatives and are typically used in combinations. Commercial examples of these additives include the Germaben II® and Kathone®.

WORKING EXAMPLES

Example 1

One novel composition of the present invention was prepared as follows from reagents as listed in Table 1 and Table 2, according to their respective weight percents in each phase. Table 1 represents the Pigment Phase and Table 2 represents the Hydrogel Phase and these two phases are mixed on about a 1:1 weight ratio to produce the topically-applied coating. Table 1 may alternatively be referred to as the Oil Phase and is prepared according to the following general procedure. Germaben II, Kathone CG, and AQ-48 were added to DI water at 46° C., held at constant temperature until dissolved, followed by cooling. Using a roto stator mixer, the pigment (~1.0 micron particles, green or brown) was added to the vessel and mixed at 15,000 rpms for 15 min. Stephan GMO, Pluracare F127, glycerin and propylene glycol were added, followed by 15 min mixing at 15,000 rpms. Other glycols in each Example that may be used include, but are not limited to, butylene glycol, 1,2 butane diol, 1,3 butane diol, or pentane diol, for example. Dow Corning 245 and 510 fluids were combined and added to the pigment composition, and a final mixing at 15,000 rpms produced the Pigment Phase.

The Hydrogel Phase was prepared as follows from the reagents in Table 2 according to their represented weight percents. Potassium monophosphate may also be added. Using an overhead stirrer at 700 rpm, DI water was added to hydrogel polymer (Pemulen TR-2) and mixed for 20 min. A concentrated stock solution of simulated sweat was prepared from water at 50° C. and the inorganic salts from Table 2, added in the order listed, NaCl, $CaCl_2$, $MgSO_4$, and $KH_2PO_4$. The sweat solution was cooled and added to hydrogel at 400 rpm. The resulting Hydrogel Phase was neutralized with an acid base titrant such as triethanolamine (TEA) to adjust the pH to about 7. The Pigment Phase and Hydrogel Phase were added in about a 1:1 ratio based on weight to produce the topically-applied coating. The composition spread evenly to produce a continuous uniform coating, which was inspected using ocular microscopy at ×100 to ×1000 magnification. Thermogravimetric analysis (TGA) under ballistic heating conditions demonstrate that hydrogel compositions will retain water under high thermal flux scenarios, FIG. 1. Cone calorimetry assay was performed under the following test conditions of 74° F., 48% RH, 80 kW/m² heat flux, 30 g/s exhaust duct flow rate, horizontal sample orientation, 2 mm thick 0.0088 m², and 8.3 g initial mass. The time to ignition (s), average heat release rate over the first 60 s (kW/m²) and the peak heat release rate (kW/m²) were 62 s, 39 kW/m², and 57 kW/m² for the ~7 wt % brown pigmented sample, and 80 s, 34 kW/m², and 50 kW/m² for the comparable wt % green pigmented sample, respectively.

Example 2

A second variation of the topically-applied coating was prepared using the Hydrogel Phase from Table 2 and a modified Pigment Phase II according to Table 3. Reagents were added in the order listed and in the defined weight percent. Hydrogel Phase and Pigment Phase II were combined as described in Example 1, and films were found to be continuous and uniform. Cone calorimetry assay was performed under the following test conditions of 74° F., 48% RH, 80 kW/m² heat flux, 30 g/s exhaust duct flow rate, horizontal sample orientation, 2 mm thick 0.0088 m², and 8.3 g initial mass. The time to ignition (s), average heat release rate over the first 60 s (kW/m²) and the peak heat release rate (kW/m²) were 65 s, 30 kW/m², and 73 kW/m² for the ~7 wt % brown pigmented sample, and 55 s, 32 kW/m², and 50 kW/m² for the comparable wt % green pigmented sample, respectively. Cone calorimetry assay was performed on a commercial sample (B.C.B. International) for comparison and produced a time to ignition (s), average heat release rate over the first 60 s (kW/m²) and the peak heat release rate (kW/m²) were 4 s, 353 kW/m², and 691 kW/m².

Figure 2:
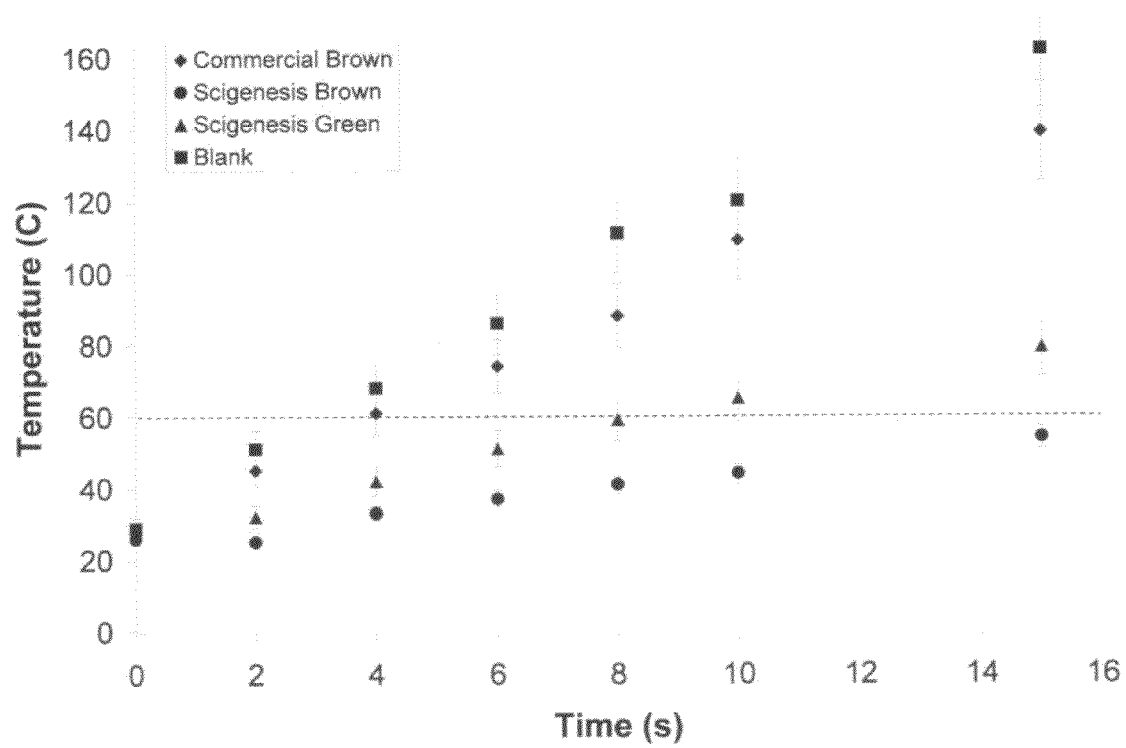
FIG. 2 is a graphical illustration of the temperature of a polished aluminum coupon measured as a function of time of exposure to the applied heat utilizing different topically-applied coatings.

An additional test was designed to evaluate sample response to thermal flux and is described as follows. The compositions of the prototype formulations of Example 2 were coated on metal coupons. The coated metal coupons were then subjected to a heat flux produced by a MAP gas burner situated four (4) inches from the surface of each coupon. An uncoated blank metal coupon was used as control, and a coupon coated in commercial BROWN camouflage paint (B.C.B. International) was included for comparison. The temperature of the metal coupon was measured as a function of time of exposure to the applied heat. The results are shown in FIG. 2.

The control and commercial Brown samples heated at a much faster rate than those treated with the prototype composition formulations. Importantly, the temperature at which skin begins to burn is about 60° C. The control and comparison samples reached this temperature in 4 seconds or less, whereas the prototype Brown sample took 10 seconds to reach this threshold temperature and the prototype Green sample had not reached 60° C. even after 15 seconds of exposure to the applied heat.

Example 3

A third variation of the topically-applied coating composition was prepared using the Hydrogel Phase from Table 2 and a modified Pigment Phase III according to Table 4. Reagents were added in the order listed and in the defined weight percent. Table 4 representing the Pigment Phase and Table 1 representing the Hydrogel Phase compositions are combined on about a 1:1 weight ratio to produce the topically-applied coating. Table 4 may be alternatively referred to as the Oil Phase and is prepared according to the following general procedure. Germaben II, propylene glycol, glycerin, and DI water are added to a beaker and mixed under high shear conditions using an overhead stirrer fitted with a Cowels blade at 2500 rpm. The pigment particles (~1.0 micron particles, white or brown) are combined in about a 1:1 weight ratio using a DVZ-F 150 speed mixer (also called a Dual Asymmetric Centrifugal Laboratory Mixer) from Flacktek USA, Inc. at 2500 rpm for a five-minute duration. The coated pigments are then added to the DI water under high shear conditions and allowed to mix at 2500 rpm for 20 minutes. Dow Corning 245 oil containing one wt % MQ resin, Dow Corning 510 oil 100 cst or Dow Corning 200 fluid 50 cst/350 cst, Silicone HL-88 and Ganex V-216 are combined for 1 minute at 2500 rpm in the speed mixer before being added to the DI water/pigment composition under high shear conditions. This is allowed to mix at 2500 rpm for 20 minutes. Upon removal from the blade, Pigment Phase III is allowed to defoam and is then combined with the Hydrogel from Table 1 in about a 1:1 weight ratio. This composition is place in the speed mixer at 2500 rpm for 20 minutes. A 25 wt % solution of AQ-38 film former is added to the topically-applied composition formulation in an appropriate amount to achieve 4 wt % solids of AQ-38. This is blended into the formulation using the speed mixer at 2500 rpm for five minutes. Films were found to be continuous and uniform. Cone calorimetry assay was performed under the following test conditions of 74° F., 48% RH, 80 kW/m$^2$ heat flux, 30 g/s exhaust duct flow rate, horizontal sample orientation, 2 mm thick 0.0088 m$^2$, and 8.3 g initial mass. The time to ignitions (s), average heat release rate over the first 60 s (kW/m$^2$), and the peak heat release rate (kW/m$^2$) were 20.3 s, 81.1 kW/m$^2$, and 225.7 kW/m$^2$, respectively, for the ~7 wt % pigmented brown sample.

SUMMARY

Protection of a substrate against a potential heat-degrading temperature rise was achieved by the surface application of the novel compositions of the present invention comprising near-IR reflective pigments and hydrogels, prepared from aqueous phases comprising water and simulated sweat salt concentrations.

The present invention has for the first time described and fully characterized novel topically-applied skin and face paint compositions, and methods of making and using such compositions, comprising cosmetic and near infrared reflecting pigments and hydrogels swollen with aqueous solution and/ or with simulated sweat so that the skin of a wearer is protected from damage due to intense external thermal flux.

The above detailed description is presented to enable any person skilled in the art to make and use the invention. Specific details have been disclosed to provide a comprehensive understanding of the present invention and are used for explanation of the information provided. These specific details, however, are not required to practice the invention, as is apparent to one skilled in the art. Descriptions of specific applications, analyses, and calculations are meant to serve only as representative examples. Various suitable changes, modifications, combinations, and equivalents to the preferred embodiments may be readily apparent to one skilled in the art and the general principles defined herein may be applicable to other embodiments and applications while still remaining within the spirit and scope of the invention. The claims and specification should not be construed to unduly narrow the complete scope of protection to which the present invention is entitled. Moreover, the terminology used herein is for the purpose of such description and not of limitation. It should also be understood that the figures are presented for example purposes only. No intention exists for the present invention to be limited to the embodiments shown and the invention is to be accorded the widest possible scope consistent with the principles and features disclosed herein.

TABLE 1

| INCI Name | Trade Name | WT % |
| --- | --- | --- |
| Deionized Water | DI water | 52.47 |
| Propylene Glycol, Diazoldinyl Urea, Methyl Paraben, and Propyl Paraben | Germaben II | 0.98 |
| Methylchloroisothiazolinone and Methylisothiazolinone | Kathon CG | 0.49 |
| Polyester 5 | Eastman AQ 48 Ultra Polymer | 2.36 |
| Pigment | Pigment | 14.00 |
| Glyceryl Mono Oleate | Stepan GMO | 1.97 |
| Ploxamer 407 | Pluracare F127 Prill | 1.97 |
| Propylene Glycol | Propylene Glycol | 0.59 |
| Glycerin | Glycerin | 0.59 |
| Cyclopentasiloxane | Dow Corning 245 Fluid | 17.21 |
| Phenylmethyl siloxane | Dow Corning 510 Fluid (100 cSt) | 7.37 |
| Total | | 100 |

TABLE 2

| Formula | Common Name | WT % |
| --- | --- | --- |
| H$_2$O | Deionized water | 93.23 |
| NaCl | Sodium Chloride | 0.51 |
| CaCl$_2$ | Calcium Chloride | 0.31 |
| MgSO$_4$ | Magnesium Sulfate | 0.02 |
| KH$_2$PO$_4$ | Potassium dihydrogen phosphate | 0.13 |
| TEA | Triethanol amine | 2.8 |
| Hydrogel polymer | Various | 3.0 |
| Total | | 100 |

TABLE 3

| INCI Name | Trade Name | WT % |
| --- | --- | --- |
| Deionized Water | DI water | 46.08 |
| Propylene Glycol, Diazoldinyl Urea, Methyl Paraben, and Propyl Paraben | Germaben II | 0.46 |
| Polyester 5 | Eastman AQ 48 Ultra Polymer | 2.91 |
| Pigment | Pigment | 13.83 |
| Ammonium nonylphenol ether sulfate | ABEX EP-110 | 13.83 |
| Propylene Glycol | Propylene Glycol | 0.46 |
| Glycerin | Glycerin | 0.46 |
| Cyclopentasiloxane | Dow Corning 245 Fluid | 15.67 |
| Phenylmethyl siloxane | Dow Corning 510 Fluid (100 cSt) | 6.3 |
| Total | | 100 |

TABLE 4

| INCI Name | Trade Name | WT % |
| --- | --- | --- |
| Deionized water | DI Water | 36.28 |
| Propylene Glycol, Diazoldinyl Urea, Methyl Paraben and Propyl Paraben | Germaben II | 0.4 |
| Propylene Glycol | Propylene Glycol | 0.4 |
| Glycerin | Glycerin | 0.4 |
| Pigment | Pigment | 14 |
| Ammonium Nonylphenol ether sulfate | Abex EP-110 | 14 |
| Cyclopentasiloxane | Dow Corning 245 fluid | 20 |
| Cyclopentasiloxane and Trimethylsiloxysilicate | Dow Corning 749 fluid | 0.02 |
| Phenylmethylsiloxane | Dow Corning 510 fluid (100 cst) | 6.5 |

TABLE 4-continued

| INCI Name | Trade Name | WT % |
|---|---|---|
| Dimethicone | HL88 | 2 |
| PVP/Hexadecene | Ganex V-216 | 2 |
| Polyester 5 | AQ-38 | 4 |
| | | 100 |

What is claimed is:

1. A topically-applied coating composition for protecting the skin of a user thereof against damage from intense external thermal flux emanating from flash fire and other intense thermal flux conditions, said composition comprising water and an effective amount of each of at least one reflective pigment and at least one hydrogel, wherein the composition provides protection against damage by maintaining the skin temperature at or below the threshold temperature of about 60° C. for at least about 10 seconds of exposure to the intense external thermal flux.

2. The composition of claim 1, wherein the at least one reflective pigment is a near infrared reflecting pigment that reflects radiated heat in the wavelength range of about 0.001 micrometers to about 5.0 micrometers.

3. The composition of claim 2, wherein the at least one hydrogel is compatible with the at least one near infrared reflecting pigment and with the user's skin perspiration.

4. The composition of claim 1, wherein the at least one hydrogel comprises at least one hydrophilic polymer swollen by water or an aqueous solution.

5. The composition of claim 4, wherein the at least one hydrogel has swellability that ranges from about 5 to 2000 times the original volume of the polymer therein.

6. The composition of claim 1, wherein the at least one hydrogel is swollen with aqueous solution, simulated sweat, or a combination thereof.

7. The composition of claim 1, further comprising at least one dispersant for aiding the dispersion of the at least one reflecting pigment.

8. The composition of claim 7, wherein the at least one dispersant is a dispersant surfactant poloxamer.

9. The composition of claim 7, further comprising at least one surfactant for aiding in spreading the composition on the skin.

10. The composition of claim 9, further comprising at least one volatile oil, at least one nonvolatile oil, at least one humectant, or at least one slip agent, or a combination thereof, for aiding in spreading the composition on the skin.

11. The composition of claim 10, further comprising at least one salt for adjusting rheology and conferring compatibility with perspiration on the skin.

12. The composition of claim 11, wherein the at least one salt is an inorganic chloride, a sulfate, a phosphate, or a combination thereof.

13. The composition of claim 10, wherein the volatile oil is a silicone oil.

14. The composition of claim 11, wherein the composition further comprises an emulsifier for emulsifying the at least one volatile oil, the at least one nonvolatile oil, or a combination thereof.

15. The composition of claim 14, wherein the emulsifier is a polymeric emulsifier, a glycerol mono-oleate, an ammonium nonylphenol ether sulfate, or a combination thereof.

16. The composition of claim 1, further comprising at least one conventional topically-applied pigment, at least one colorant, or a combination thereof.

17. The composition of claim 16, wherein the at least one pigment is a cosmetic pigment, a near infrared reflecting pigment, or a combination thereof.

18. The composition of claim 1, wherein the composition is removable from the skin by flushing with a nonirritant fluid.

19. The composition of claim 1, wherein the composition simultaneously reflects heat away from the skin of a user thereof and diverts thermal energy to a complementary evaporative cooling mechanism.

20. A topically-applied coating composition for protecting the skin of a user thereof against damage from intense external thermal flux emanating from flash fire and other intense thermal flux conditions, said composition comprising water and an effective amount of at least one reflecting pigment and an effective amount of at least one hydrogel and comprising a pigment phase and a hydrogel phase, wherein the pigment phase is mixed on about a 1:1 weight basis with the hydrogel phase comprising about 3 weight percent of hydrogel polymer in a simulated sweat solution and wherein the composition provides protection against damage by maintaining the skin temperature at or below the threshold temperature of about 60° C. for at least about 10 seconds of exposure to the intense external thermal flux.

21. The composition of claim 20, wherein the simulated sweat solution comprises an effective amount of chloride, sulfate, phosphate inorganic salt, or a combination thereof.

22. The composition of claim 20, wherein the composition further comprises an effective amount of each of a reflecting pigment, oil, hydrogel, and film former to prevent skin injury from radiant heat.

23. The composition of claim 22, wherein the film former provides a continuous film within the cosmetic topically-applied composition or, optionally, provides a transfer-resistant film within the topically-applied coating composition.

24. The composition of claim 22, wherein the composition further comprises an effective amount of each of water, glycol, surfactant, glycerin, preservative, and pigment, and wherein the glycol is propylene glycol, butylene glycol, 1,2 butane diol, 1,3 butane diol, pentane diol, or a combination thereof.

25. The composition of claim 22, wherein the oil comprises a silicone oil.

26. The composition of claim 22, wherein the hydrogel is prepared in a simulated sweat solution and comprises an effective amount of each of hydrogel polymer, water, chloride, sulfate, phosphate inorganic salt, and acid base titrant.

27. The composition of claim 22, wherein the film former comprises at least one sulfopolyester polymer, at least one hydrophobic polylactam polymer, or a combination thereof.

28. The composition of claim 22, wherein the composition further comprises at least one antimicrobial agent, at least one preservative, or a combination thereof.

29. The composition of claim 20, further comprising at least one conventional topically-applied pigment, at least one colorant, or a combination thereof.

30. The composition of claim 29, wherein the at least one pigment is a cosmetic pigment, a near infrared reflecting pigment, or a combination thereof.

31. A process for preparing a skin protecting topically-applied coating composition which comprises mixing a composition according to claim 1 with at least one hydrogel that is formed from at least one hydrophilic polymer and optionally with an effective amount of at least one topically-applied pigment.

32. The process of claim 31, further comprising optionally mixing with the composition at least one colorant.

33. The process of claim 32, wherein the at least one pigment is a cosmetic pigment, a near infrared reflective pigment, or a combination thereof.

34. The composition of claim 20, wherein the at least one hydrogel comprises at least one hydrophilic polymer swollen by water or an aqueous solution.

35. The composition of claim 20, wherein the at least one hydrogel is swollen with aqueous solution, simulated sweat, or a combination thereof.

36. The composition of claim 20, wherein the at least one hydrogel is prepared in a sweat solution and comprises an effective amount of each of hydrogel polymer, water, chloride, sulfate, phosphate inorganic salt, and acid base titrant.

37. The composition of claim 20, wherein the simulated sweat solution comprises an effective amount of each of sodium chloride, calcium chloride, magnesium sulfate, and potassium monophosphate.

38. The composition of claim 20, further comprising at least one conventional topically-applied pigment, at least one colorant, or a combination thereof.

39. The composition of claim 38, wherein the at least one pigment is a cosmetic pigment, a near infrared reflective pigment, or a combination thereof.

40. A method of producing a topically-applied coating composition according to claim 1 for protecting the skin of a user thereof against damage from external thermal flux, the method comprising mixing reagents to form a pigment phase and a hydrogel phase, wherein the pigment phase and the hydrogel phase are mixed on about a 1:1 weight ratio.

41. The method of claim 40, wherein the hydrogel phase optionally includes a simulated sweat solution comprising water and at least one inorganic salt.

42. The method of claim 40, wherein the hydrogel phase is neutralized to a pH of about 7.0.

43. The method of claim 40, wherein the reagents that form the hydrogel phase are effective amounts of each of deionized water, sodium chloride, calcium chloride, magnesium sulfate, potassium dihydrogen phosphate, potassium monophosphate, triethanol amine, and at least one hydrogel polymer.

44. The method of claim 40, wherein the reagents that form the pigment phase are effective amounts of each of deionized water, at least one co-solvent, a film former, at least one pigment, at least one emulsifier, at least one volatile oil, and at least one non-volatile oil.

45. The method of claim 40, wherein the reagents that form the pigment phase are effective amounts of each of deionized water, at least one co-solvent, a film former, at least one pigment, at least one emulsifier, at least one volatile oil, at least one non-volatile oil, and at least one preservative.

46. The method of claim 45, wherein the at least one preservative is selected from the reagent group of classes consisting of diazoldinyl ureas, methyl parabens, propyl parabens, methychloroisothiazolinones, and methylisothiazolinones.

47. The method of claim 40, wherein the reagents that form the pigment phase are effective amounts of each of deionized water, glycol, diazoldinyl urea, methyl paraben, propyl paraben, polyester 5, at least one pigment, ammonium nonylphenol ether sulfate, glycerin, cyclopentasiloxane, and phenylmethyl siloxane, and wherein the glycol is propylene glycol, butylene glycol, 1,2 butane diol, 1,3 butane diol, pentane diol, or a combination thereof.

48. The method of claim 40, wherein the reagents that form the pigment phase are effective amounts of each of deionized water, glycol, diazoldinyl urea, methyl paraben, propyl paraben, polyester 5, at least one pigment, ammonium nonylphenol ether sulfate, glycerin, cyclopentasiloxane, phenylmethyl siloxane, trimethylsiloxysilicate, dimethicone, polyvinyl pyrrolidone, and hexadecane, and wherein the glycol is propylene glycol, butylene glycol, 1,2 butane diol, 1,3 butane diol, pentane diol, or a combination thereof.

49. The method of claim 40, wherein the pigment phase includes a cosmetic pigment, a near infrared reflective pigment, or a combination thereof.

50. A method of protecting the skin of a user in need thereof against damage from external thermal flux, which comprises applying a composition as defined in claim 1 to the skin of the user.

51. A method of protecting the skin of a user in need thereof against damage from external thermal flux, which comprises applying a composition as defined in claim 20 to the skin of the user.

* * * * *